United States Patent [19]
Gerdes

[11] Patent Number: 5,989,813
[45] Date of Patent: *Nov. 23, 1999

[54] DETECTION OF AMPLIFIED NUCLEIC ACID SEQUENCES USING BIFUNCTIONAL HAPTENIZATION AND DYED MICROPARTICLES

[75] Inventor: John C. Gerdes, Denver, Colo.

[73] Assignee: Molecular Innovations, Inc., Denver, Colo.

[*] Notice: This patent issued on a continued prosecution application filed under 37 CFR 1.53(d), and is subject to the twenty year patent term provisions of 35 U.S.C. 154(a)(2).

[21] Appl. No.: 08/664,863

[22] Filed: Jun. 17, 1996

Related U.S. Application Data

[60] Provisional application No. 60/002,245, Jul. 13, 1995.

[51] Int. Cl.$^6$ .............. C12Q 1/68; C12Q 19/34; C07H 21/04; C07H 21/00
[52] U.S. Cl. .............. 435/6; 435/91.2; 536/24.3; 536/25.3
[58] Field of Search .............. 435/91.2; 536/24.3, 536/25.3

[56] References Cited

U.S. PATENT DOCUMENTS

| | | | |
|---|---|---|---|
| 4,683,195 | 7/1987 | Mullis et al. | 435/91 |
| 4,683,202 | 7/1987 | Mullis et al. | 435/6 |
| 4,687,732 | 8/1987 | Ward et al. | 435/6 |
| 4,965,188 | 10/1990 | Mullis et al. | 435/6 |
| 5,168,044 | 12/1992 | Joyce | 435/7.24 |
| 5,232,829 | 8/1993 | Longiaru | 435/29 |
| 5,328,825 | 7/1994 | Warren, III et al. | 435/6 |
| 5,344,757 | 9/1994 | Holtke et al. | 435/6 |
| 5,374,524 | 12/1994 | Miller | 435/6 |
| 5,387,510 | 2/1995 | Wu | 435/91.2 |
| 5,415,839 | 5/1995 | Zaun et al. | 422/64 |
| 5,455,166 | 10/1995 | Walker | 435/91.2 |
| 5,489,507 | 2/1996 | Chehab | 435/6 |
| 5,527,673 | 6/1996 | Reinhartz et al. | 435/6 |
| 5,541,069 | 7/1996 | Mortenson et al. | 435/7.9 |
| 5,543,305 | 8/1996 | Cummins et al. | 435/91.1 |

FOREIGN PATENT DOCUMENTS

| | | | |
|---|---|---|---|
| 063879 | 4/1982 | European Pat. Off. | C07H 19/20 |
| 320308 | 12/1988 | European Pat. Off. | C12Q 1/68 |

OTHER PUBLICATIONS

Watson, J.D. et al. (1987) Molecular Biology of the Gene, 4th Ed., pp. 299–301, Benjamin/Cummings Pub. Menlo Park, CA.
Gerdes et al. (1993) Transplantation Proceedings 25:1411.

Primary Examiner—Ardin H. Marschel
Assistant Examiner—Joyce Tung
Attorney, Agent, or Firm—Julie L. Bernard, P.C.

[57] ABSTRACT

The invention describes an assay for detecting amplified target nucleic acid sequences with a visual signal. The sensitivity and specificity of the methodology are based on bifunctional target labeling during the amplification step or subsequent hybridization that generates a bifunctional label. The invention may be used, for example, in the screening of amplicon detection for the purpose of more efficiently screening libraries. The invention is also useful to detect nucleic acid sequences indicative of a genetic defect or contagious disease when used with the appropriate primers, as well as detect the existence of nucleic acid amplification.

30 Claims, 6 Drawing Sheets

SEQUENCE LISTING (1) GENERAL INFORMATION:

(iii) NUMBER OF SEQUENCES:    13

(2) INFORMATION FOR SEQ ID NO:1:

(i) SEQUENCE CHARACTERISTICS:
        (A) LENGTH:   27 bases
        (B) TYPE:     nucleic acid
        (C) STRANDEDNESS:  single
        (D) TOPOLOGY: linear (ix) SEQUENCE DESCRIPTION:    SEQ ID NO:1:

ATAATCCACC TATCCCAGTA GGAGAAA                                        27

(2) INFORMATION FOR SEQ ID NO:2:

(i) SEQUENCE CHARACTERISTICS:
        (A) LENGTH:   28 bases
        (B) TYPE:     nucleic acid
        (C) STRANDEDNESS:  single
        (D) TOPOLOGY: linear (ix) SEQUENCE DESCRIPTION: SEQ ID NO:2:

TTTGGTCCTT GTCTTATGTC CAGAATGC                                              28

(2) INFORMATION FOR SEQ ID NO:3:

(i) SEQUENCE CHARACTERISTICS:
              (A) LENGTH:   115 bases
              (B) TYPE:     nucleic acid
              (C) STRANDEDNESS: single
              (D) TOPOLOGY: linear (ix) SEQUENCE DESCRIPTION: SEQ ID NO:3:

ATAATCCACC TATCCCAGTA GGAGAAATTT ATAAAAGATG                                  40

GATAATCCTG GGATTAAATA AAATAGTAAG AATGTATAGC                                  80

CCTACCAGCA TTCTGGACAT AAGACAAGGA CCAAA                                      115

(2) INFORMATION FOR SEQ ID NO:4:

(i) SEQUENCE CHARACTERISTICS:
              (A) LENGTH:   24 bases
              (B) TYPE:     nucleic acid
              (C) STRANDEDNESS: single
              (D) TOPOLOGY: linear (ix) SEQUENCE DESCRIPTION: SEQ ID NO:4:

GCATTGAGGA GATCTGCATG AAGG                                                   24

(2) INFORMATION FOR SEQ ID NO:5:

(i) SEQUENCE CHARACTERISTICS:
              (A) LENGTH:   24 bases
              (B) TYPE:     nucleic acid
              (C) STRANDEDNESS: single
              (D) TOPOLOGY: linear (ix) SEQUENCE DESCRIPTION: SEQ ID NO:5:

ATTACTGAGG ACAGAGGGAT AGTC                                                   24

(2) INFORMATION FOR SEQ ID NO:6:

(i) SEQUENCE CHARACTERISTICS:
              (A) LENGTH:   61 bases
              (B) TYPE:     nucleic acid
              (C) STRANDEDNESS: single
              (D) TOPOLOGY: linear (ix) SEQUENCE DESCRIPTION: SEQ ID NO:6:

GCTGGTAGGG CTATACATTC TTACTATTTT ATTTAATCCC                                  40

AGGATTATCC ATCTTTTATA A                                                     61

(2) INFORMATION FOR SEQ ID NO:7:

(i) SEQUENCE CHARACTERISTICS:
              (A) LENGTH:   20 bases
              (B) TYPE:     nucleic acid
              (C) STRANDEDNESS: single
              (D) TOPOLOGY: linear (ix) SEQUENCE DESCRIPTION: SEQ ID NO:7:

AAAGATGTag agGGTACAGA                                                       20

(2) INFORMATION FOR SEQ ID NO:8:

(i) SEQUENCE CHARACTERISTICS:
        (A) LENGTH:    24 bases
        (B) TYPE:      nucleic acid
        (C) STRANDEDNESS: single
        (D) TOPOLOGY: linear (ix) SEQUENCE DESCRIPTION:    SEQ ID NO:8:

AATCTGTACC CTCTACATCT TTAA                                                  24

(2) INFORMATION FOR SEQ ID NO:9:

(i) SEQUENCE CHARACTERISTICS:
        (A) LENGTH:    15 bases
        (B) TYPE:      nucleic acid
        (C) STRANDEDNESS: single
        (D) TOPOLOGY: linear (ix) SEQUENCE DESCRIPTION:    SEQ ID NO:9:

CGATCGAGCA AGCCA                                                            15

(2) INFORMATION FOR SEQ ID NO:10:

(i) SEQUENCE CHARACTERISTICS:
        (A) LENGTH:    15 bases
        (B) TYPE:      nucleic acid
        (C) STRANDEDNESS: single
        (D) TOPOLOGY: linear (ix) SEQUENCE DESCRIPTION:    SEQ ID NO:10:

CGAGCCGCTC GCTGA                                                            15

(2) INFORMATION FOR SEQ ID NO:11:

(i) SEQUENCE CHARACTERISTICS:
        (A) LENGTH:    40 bases
        (B) TYPE:      nucleic acid
        (C) STRANDEDNESS: single
        (D) TOPOLOGY: linear (ix) SEQUENCE DESCRIPTION:    SEQ ID NO:11:

ACCGCATCGA ATGCATGTCT CGGGTAAGGC GTACTCGACC                                 40

(2) INFORMATION FOR SEQ ID NO:12:

(i) SEQUENCE CHARACTERISTICS:
        (A) LENGTH:    40 bases
        (B) TYPE:      nucleic acid
        (C) STRANDEDNESS: single
        (D) TOPOLOGY: linear (ix) SEQUENCE DESCRIPTION:    SEQ ID NO:12:

CGATTCCGCT CCAGACTTCT CGGGTGTACT GAGATCCCCT                                 40

(2) INFORMATION FOR SEQ ID NO:13:

(i) SEQUENCE CHARACTERISTICS:
        (A) LENGTH:    91 bases
        (B) TYPE:      nucleic acid
        (C) STRANDEDNESS: single
        (D) TOPOLOGY: linear (ix) SEQUENCE DESCRIPTION:    SEQ ID NO:13:

TGGACCCGCC AACAAGAAGG CGTACTCGAC CTGAAAGACG                                 40

TTATCCACCA TACGGATAGG GGATCTCAGT ACACATCGAT                                 80

CCGGTTCAGC G                                                                91

DETECTION OF AMPLIFIED NUCLEIC ACID SEQUENCES USING BIFUNCTIONAL HAPTENIZATION AND DYED MICROPARTICLES

RELATED APPLICATIONS

This application claims priority to provisional patent application Ser. No. 60/002245, filed Jul. 13, 1995.

FIELD OF INVENTION

This invention relates to the general fields of molecular biology and medical sciences, and specifically to the detection of amplified nucleic acid sequences. This application, thus, describes a method of detecting amplified nucleic acid sequences rapidly and accurately using bifunctional humanization and dyed microparticles. This application further relates to a test kit useful for improved detection of amplified nucleic acids.

BACKGROUND AND PRIOR ART

In current research and development process involving process involving nucleic acid (DNA and RNA) amplifications, there is a need for rapid, accurate qualitative determination of the results from such experiments. Traditionally, such determinations require the preparation of gels, for example, agarose, for electrophoresis of amplified nucleic acids and the use of a nucleic acid intercalating agent, for example, ethidium bromide, which is fluorescent under ultraviolet light. Generally, agarose gels are cast by melting a measured amount of agarose in a buffer resulting in a transparent solution. The melted agarose is poured into a mold and allowed to harden. The mold includes sample wells for adding the nucleic acids to be analyzed. In order to detect the nucleic acid, ethidium bromide is included in the buffer used to prepare the gel or the gel is stained with ethidium bromide after electrophoresis. Samples of the nucleic acids to be analyzed are mixed with a loading buffer and deposited into the sample wells. The gel is then subjected to a certain applied voltage resulting in the lateral migration of the nucleic acid through the gel. This method requires a power supply and an apparatus for casting and running the gels. Additionally, an ultraviolet light box is required for detecting the nucleic acid, requiring the use of protective eye wear. Further, the use of ethidium bromide poses an health hazard as it is a carcinogen, a powerful mutagen and moderately toxic. The qualitative determination process, as described above, is time consuming, requires special precautions for the handling and disposing of ethidium bromide, requires the purchase of specialized equipment, poses a potential health hazard and requires specialized training in the use of the necessary equipment. The sensitivity of the method is low and since equipment is used many times over, the possibility of contamination is also present.

The introduction of nucleic acid probe tests based on hybridization into routine clinical laboratory procedures has been hindered by lack of sensitivity when compared with conventional culture techniques and immunoassays. To increase sensitivity, radioactive labels are used. The problem with the use of such radioactive labels is the laboratory management of radioisotopes and the disposal thereof. To some degree, non-isotopic labels are used to overcome this problem. However, non-isotopic methods do not possess adequate sensitivity and are cumbersome and laborious to run. In order to achieve the sensitivity needed for diagnostics, the incubation times of the current methodologies must be long, taking up to several hours or days. The current non-isotopic methodologies also employ many steps, requiring previous training and expertise.

The ability to amplify nucleic acids from clinical samples has greatly advanced nucleic acid probe technology, providing the sensitivity lacking in earlier versions of non-isotopic assays. The sensitivity afforded by oligonucleotide probe tests utilizing nucleic acid amplification now exceeds that of any other method. However, the method is still time consuming, requiring the use of specialized hybridization techniques and equipment, transfer to solid phases and specialized detection equipment.

The detection of amplified nucleic acids for clinical use largely relies on hybridization of the amplified product with a detection probe that is labeled with a variety of enzymes and luminescent reagents. U.S. Pat. No. 5,374,524 to Miller, describes a nucleic acid probe assay which combines nucleic acid amplification and solution hybridization using capture and reporter probes. These techniques require multiple reagents, several washing steps, and specialized equipment for detection of the target nucleic acid. Moreover, these techniques are labor intensive and require technicians with expertise in molecular biology.

The use of probes comprised of oligonucleotide sequences bound to microparticles is well known and illustrated in the prior art. The mechanism for attachment of oligonucleotides to microparticles in hybridization assays and for the purification of nucleic acids is also well known. European Patent No. 200 133 describes the attachment of oligonucleotides to water-insoluble particles less than 50 micrometers in diameter used in hybridization assays for the capture of target nucleotides. U.S. Pat. No. 5,387,510 to Wu, describes the use of oligonucleotide sequences covalently bound to microparticles as probes for capturing PCR amplified nucleic acids. U.S. Pat. No. 5,328,825 to Findlay also describes an oligonucleotide linked by way of a protein or carbohydrate to a water-insoluble particle. The oligonucleotide probe is covalently coupled to the microparticle or other solid support. The sensitivity and specificity of the four above-reference patents, each of which is specifically incorporated herein, is based on hybridization of the oligonucleotide probe to the target nucleic acid.

The use of incorporated non-radioactive labels into the amplification reactions for the detection of nucleic acids is also well known in the art. Nucleic acids modified with biotin (U.S. Pat. No. 4,687,732 to Ward et al.; European Patent No. 063879; both specifically incorporated herein), digoxin (European Patent No. 173251, specifically incorporated herein) and other haptens have also been used. For example, U.S. Pat. No. 5,344,757 to Graf, specifically incorporated herein, uses a nucleic acid probe containing at least one hapten as a label for hybridization with a complementary target nucleic acid bound to a solid membrane. The sensitivity and specificity of these assays is based on the incorporation of a single label in the amplification reaction which can be detected using an antibody specific to the label. The usual case involves an antibody conjugated to an enzyme. Furthermore, the addition of substrate generates a colorimetric or fluorescent change which can be detected with an instrument.

Still, the above-described approaches are labor intensive with many steps and washes; require special and costly equipment for the detection of the target nucleic acid; require trained staff; and take a several hours to complete. Several patents have issued which deal with automation of the processes of amplification and subsequent detection of the amplicon. These patents use specialized equipment and are still based on the principle of hybridization and immunoassay technology. For example, European Patent No. 320308, specifically incorporated herein, describes a system for detecting target nucleic acids amplified by the ligase chain reaction.

Automated approaches eliminate the need for specially trained personnel, however, the cost of the equipment is very high and the possibility of contamination still exits since many samples will be processed by the same equipment.

The use of bifunctional labels for detection of an amplified target sequence has been explored using the ligase chain reaction (European Patent No. 320308, supra). Upon completion of the amplification by the ligation process, double stranded DNA is formed with biotin bound at one end and fluorescein bound at the other end. The labeled nucleic acid serves as an analyte in a two site immunometric assay. That is, a microparticle coated with anti-fluorescein antibodies captures the ligated product; after a wash step, a second biotin specific antibody labeled with alkaline phosphatase binds to the biotin yielding a fluorescent signal when incubated with a suitable substrate. The signal can be read with a fluourmeter. This system is based on immunometric technology and requires specialized equipment for detection of the target nucleic acid.

SUMMARY OF INVENTION

This invention is based on a novel concept for a method for detecting specific DNA or RNA sequences. The present invention is defined by agglutination through the linking of microparticles with two distinct haptens, and alternatively, by linking microparticles to a capture zone on a lateral flow membrane or a filtration membrane with two distinct haptens.

The present invention is applicable to the detection of all nucleic acids and derivatives thereof. The present invention is useful to identify specific nucleic acid sequences associated with certain diseases or conditions, to screen amplicon detection for more efficient library screening and to detect the existence of amplification, but is not intended to be limited to these uses. This invention includes a detection system for any amplification-based diagnostic.

The present invention is a method for amplification and detection of a specific target nucleic acid comprising denaturing a double stranded nucleic acid and amplifying the target enzymatically with hapten derivatized complementary primers and dNTPs, forming a water-insoluble product of said amplified target nucleic acid and detecting the resulting product.

In one embodiment of this invention, nucleic acid detection by microparticle agglutination is accomplished by amplifying, by polymerase chain reaction (PCR), a specific sequence of the cytomegalovirus genome using biotin and digoxigenin primers.

Another embodiment of this invention, combining bifunctionality and microparticle technology, is directed toward the creation of a visible line of detection on a lateral flow assay.

Other features and advantages of the present invention will become apparent from the following detailed description, taken in conjunction with the accompanying figures, that illustrate by way of example, the principles of the instant invention.

The file of this patent contains at least one figure executed in color. Copies of this patent with color figure(s) will be provided by the Patent and Trademark Office upon request and payment of the necessary fee.

BRIEF DESCRIPTION OF THE FIGURES

FIG. 8A depicts the results of lateral flow membrane assays of bifunctionally labeled Human Immunodeficiency Virus (HIV) amplification product; a visible line of detection is not present in the negative control results.

FIG. 8B depicts the results of lateral flow membrane assays of bifunctionally labeled Human Immunodeficiency Virus (HIV) amplification product; positive results are shown as a visible line of colored microparticles captured on the membrane.

DETAILED DESCRIPTION OF THE PREFERRED EMBODIMENT

Figure 1:
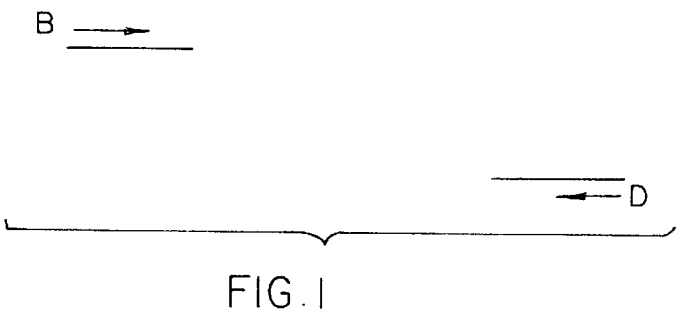
FIG. 1 illustrates the denatured nucleic acid target to be amplified with one primer 5' labeled with biotin and a second primer 5' labeled with digoxigenin.

It is to be understood that both the foregoing general description and the following detailed description are exemplary and explanatory only and are not restrictive of the invention as claimed.

The present invention describes a method for the detection of nucleic acids. The present invention is embodied in a method of detecting an amplified target nucleic acid sequence that is present in a sample. The skilled artisan recognizes that assays for a broad range of target nucleic acid sequences present in a sample may be performed in accordance with the present invention. Samples may include biological samples derived from agriculture sources, bacterial and viral sources, and from human or other animal sources, as well as other samples such as waste or drinking water, agricultural products, processed foodstuff, air, etc. Examples include blood, stool, sputum, mucus, serum, urine, saliva, teardrop, a biopsy sample, an histological tissue sample, a tissue culture product, an agricultural product, waste or drinking water, foodstuff, air, etc. The present invention is useful for the detection of nucleic acid sequences indicative of genetic defects or contagious diseases.

The following definitions will be helpful in understanding the specification and claims. The definitions provided herein should be borne in mind when these terms are used in the following examples and throughout the instant application.

As used herein, the term "target" nucleic acid molecule refers to the nucleic acid molecule that is to be amplified by the disclosed methodology. The "target" molecule can be present in a purified, partially purified or unpurified state in the sample.

As used in this invention, the term "amplification" refers to a "template-dependent process" that results in an increase in the concentration of a nucleic acid sequence relative to its initial concentration. A "template-dependent process" is a process that involves the "template-dependent extension" of a "primer" molecule. A "primer" molecule refers to a sequence of a nucleic acid which is complementary to a known portion of the target sequence and labeled with a hapten. A "template dependent extension" refers to nucleic acid synthesis of RNA or DNA wherein the sequence of the newly synthesized strand of nucleic acid is dictated by the rules of complementary base pairing of the target nucleic acid and the primers.

The present invention relates to the amplification of one specific nucleic acid sequence, resulting in a nucleic acid duplex with discrete hapten labels derivatized to each of the 5' ends or in the case of amplification by the ligase chain reaction, discrete haptens labeled on the 5' and 3' ends.

A second embodiment relates to the use of hybridization technology to create a bifunctionally labeled product. The probe may be singly labeled and designed to generate bifunctional label when combined with primer that is labeled or the probe itself may be bifunctionally labeled. This embodiment is useful under certain isothermal amplification conditions.

Figure 2:
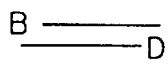
FIG. 2 shows the double strand PCR product resulting from amplification of the target nucleic acid sequence with the labeled primers.

In the most preferred embodiment of the invention, a denatured target nucleic acid is amplified and 5' primer labeled, as illustrated in FIG. 1. The first primer consists of a short nucleic acid sequence complementary to a sequence on the target nucleic acid and a biotin label on the 5' end. The second primer consists of a nucleic acid sequence which is complementary to a second sequence on the target nucleic acid and a digoxigenin label on the 5' end. The results of amplifying the target nucleic acid with the primers in a template dependent extension reaction are shown in FIG. 2.

Figure 3:
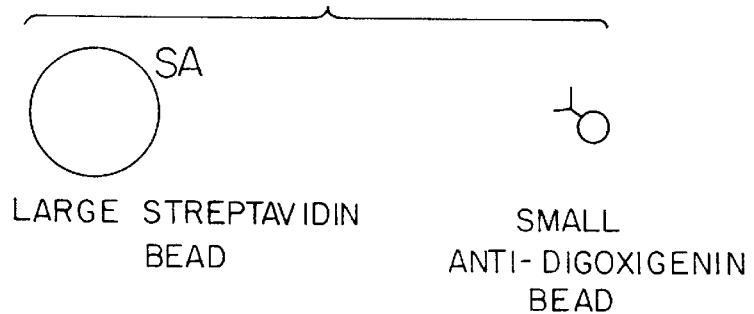
FIG. 3 illustrates large microparticles conjugated with streptavidin and small microparticles conjugated with anti-digoxigenin antibody.
Figure 4:
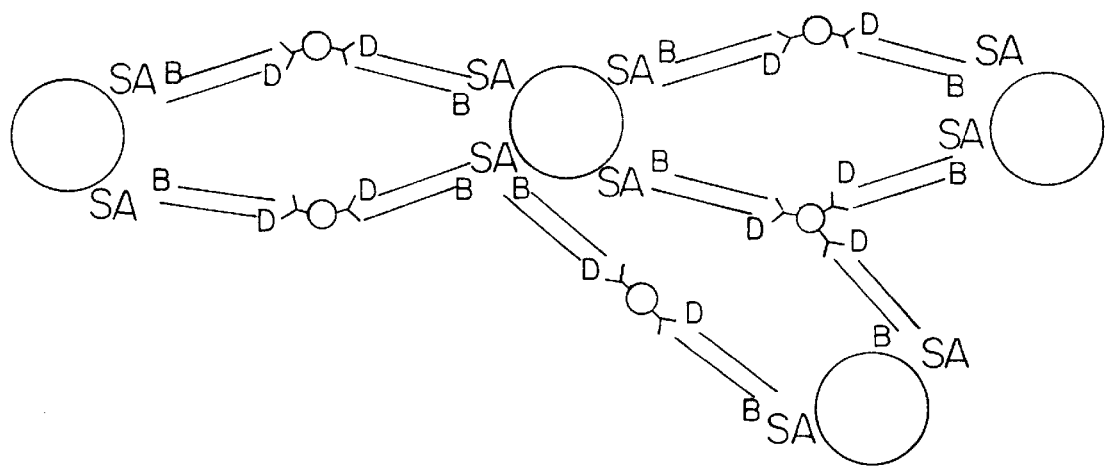
FIG. 4 illustrates the cross-linking and agglutination reaction in the presence of the amplified nucleic acid target sequence.

In this embodiment, biotin and digoxigenin are incorporated onto the 5' ends of the resulting nucleic acid. FIG. 3 shows large dyed microparticles conjugated with streptavidin and small dyed microparticles conjugated with anti-digoxigenin antibody, while FIG. 4 illustrates the results of combining the amplified nucleic acid containing the biotin and digoxigenin labels with large dyed microparticles conjugated with streptavidin and small dyed microparticles conjugated with anti-digoxigenin antibody. The result is a linear and three dimensional cross-linking of the microparticles and labeled nucleic acid, thereby detecting the amplified nucleic acid sequence.

Figure 5:
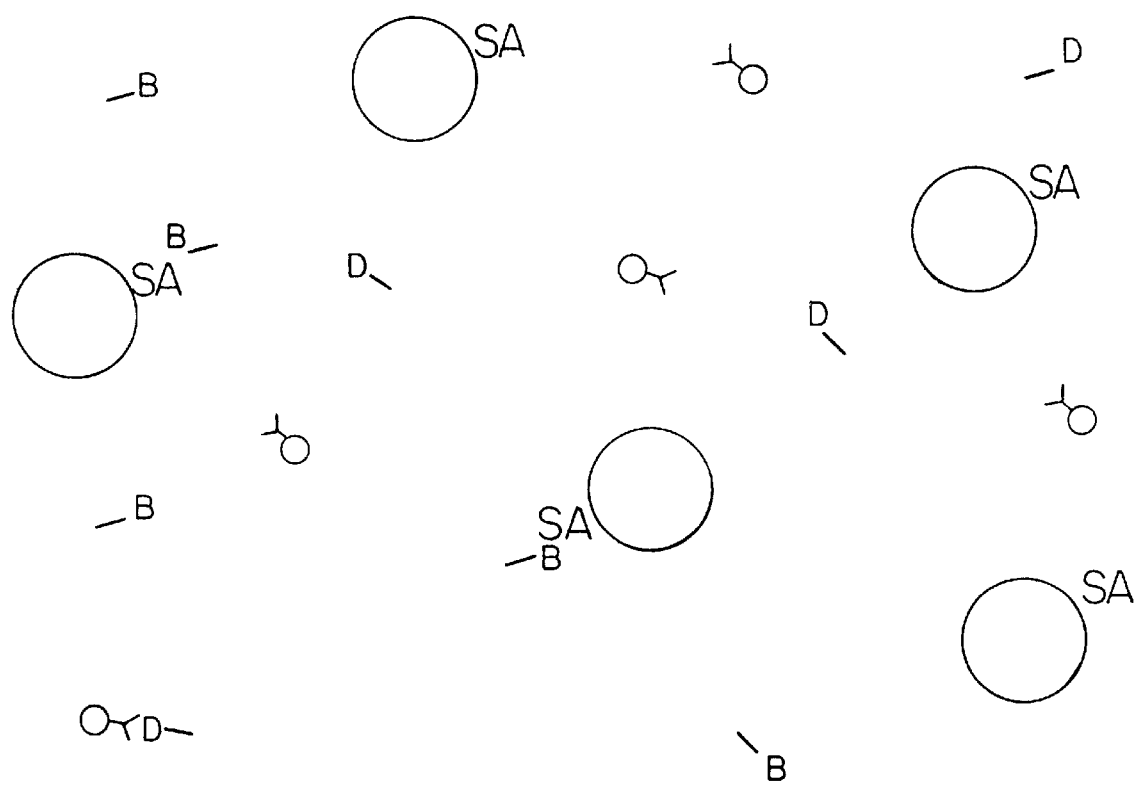
FIG. 5 illustrates the assay results in the absence of an amplified target nucleic acid in the sample.

The results of a negative sample combined with the large dyed microparticles conjugated with streptavidin and small dyed microparticles conjugated with anti-digoxigenin antibody are shown in FIG. 5. Since the target nucleic acid is not present in the sample, it cannot bind the primers required for the amplification process. The result is that some biotin derivatized primer will bind to the large dyed microparticles conjugated with streptavidin. Some digoxigenin derivatized primer will bind to the small dyed microparticles conjugated with anti-digoxigenin antibody. However, there is no linear or three dimensional cross-linking of the microparticles because the amplified nucleic acid is not present.

Accordingly, several objects and advantages of the invention described herein include: the rapid and accurate detection of amplified nucleic acid sequences with or without the use of hybridization and elaborate detection equipment; the assay disclosed herein is easy to perform, requiring little expertise in the art of molecular biology; the cost is significantly less than other methods known in the art; and the time frame for detecting an amplified sequence is cut drastically. As a research tool, this invention eliminates the need for preparing and running agarose gels to determine if a particular amplification method is successful. It may also be used in research in the screening of amplicon detection for the purpose of more efficiently screening libraries. As a diagnostic tool, the results are available a few minutes after amplification instead of hours or days. There is no danger from potential health hazards such as radioisotopes and ethidium bromide. The assay does not require special waste disposal procedures. The reagents employed are universal, meaning that the detection system in this invention can be used with any amplified nucleic acid containing bifunctional haptens specific for the receptor microparticles. The requirement for many washes in a immunometric or hybridization approach are eliminated.

Nucleic acid probe technology has developed rapidly in recent years as the scientific community has discovered its value in the detection of various diseases, organisms or genetic features. Amplification techniques provide the sensitivity to qualitatively determine the presence of even minute quantities of nucleic acid.

The invention disclosed herein relates generally to a detection method to qualitatively detect nucleic acid sequences which have been amplified from a selected target. This invention relies on the principles of bifunctional labeling of target nucleic acid during the amplification process, ligand-receptor binding, and microparticle technology for visible detection of amplified nucleic acid. The detection reaction is between the bifunctional haptens on the amplicon and dyed microparticles conjugated with ligands specific for binding to each hapten.

The sensitivity and specificity of the process described herein does not necessarily rely on hybridization of the target nucleic acid with an oligonucleotide probe. The detection system is not fluorescent or enzyme based. The sensitivity and specificity of this invention depends on the incorporation of two distinct hapten labels during the amplification step or subsequent hybridization that generates a bifunctional label. If both haptens are not present the target nucleic acid will not be detected.

The process according to the present invention is suitable for the qualitative determination of all nucleic acid amplicons. The sensitivity and accuracy of this process is improved compared to the processes currently used by those skilled in the art. The invention offers the possibility of rapid and reliable qualitative determination of the presence of amplified target nucleic acids with simple reagents.

The following examples serve to explain and illustrate the present invention. Said examples are not to be construed as limiting of the invention in anyway. Various modifications are possible within the scope of the invention.

EXAMPLE 1

Derivatization and Labeling

The present invention employs a variety of different enzymes to accomplish amplification of the target nucleic acid sequence. These enzymes are called polymerases and ligases. Polymerases are defined by their function of incorporating nucleoside triphosphates to extend a 3' hydroxyl terminus of a "primer molecule." As used herein, a "primer" is an oligonucleotide, that when hybridized to a target nucleic acid molecule, possesses a 3' hydroxyl terminus that can be extended by a polymerase and a hapten label at or near the 5' terminus. For a general discussion concerning polymerases, see Watson, J. D. et al, (1987) *Molecular Biology of the Gene*, 4th Ed., W. A. Benjamin, Inc., Menlo Park, Calif. Examples of polymerases that can be used in accordance with the methods described herein include, but are not limited to, *E.coli* DNA polymerase I, the large proteolytic fragment of *E. coli* polymerase I, commonly known as "Klenow" polymerase, Taq-polymerase, T7 polymerase, T4 polymerase, T5 polymerase and reverse transcriptase. The ligase chain reaction, described in European Patent No. 320308, uses 4 nucleic acid oligonucleotides that hybridize to the denatured target sequence, two on each strand (A and B), adjacent to one another and complementary to the two primers which hybridize with the other strand (A' and B'). After hybridization, the two primers on each strand are joined with the enzyme, DNA ligase. In this embodiment of the invention, each oligonucleotide A and B' is derivatized with hapten ($H_1$) on the 3' end and A' and B would need to be derivatized with hapten ($H_2$) on the 5' end. The resulting double stranded product will be labeled with ($H_1$) and ($H_2$).

In the present invention, polymerases with the capacity to continue the extension of a particular primer to produce a double stranded extension product with discreet hapten labels on each of the 5' ends are preferred. The general principles and conditions for amplification of nucleic acids using polymerase chain reaction are quite well known, the details of which are provided in numerous references including U.S. Pat. No. 4,683,195, U.S. Pat. No. 4,683,202 and U.S. Pat. No. 4,965,188, all to Mullis et al., all of which are specifically incorporated herein. Thus, the details of PCR technology are not included herein. However, in view of the teaching in the art and the specific teaching provided herein, a skilled artisan is able to practice the present invention by making only minor adjustments, as outlined herein, in order to accomplish the advantages of detection utilizing this system.

The oligonucleotide primers ($P_1$ and $P_2$) used in this invention contain at least one hapten, as label, which does not participate in the priming reaction. The hapten is bound to at least one position of the nucleic acid primer. For the derivatization of nucleic acid primers, various methods can be employed. (Sambrook et al. (1989) *Molecular Cloning: A Laboratory Manual*, 2nd Ed., Cold Spring Harbor Laboratory, Cold Spring Harbor, N.Y.). The incorporation of the hapten can take place enzymatically, chemically or photochemically. The hapten can be derivatized directly to the 5' end of the primer or contain a bridge 1 to 30 atoms long. In the preferred embodiment, the bridge is linear. However, in a further embodiment, the bridge consists of a branched chain with a hapten molecule on at least one of the chain ends. By means of the presence of several hapten molecules on the ends of a branched chain, the detection sensitivity is increased. The preferred haptens for this invention are biotin ($H_1$) and digoxigenin ($H_2$), however, any other hapten which has available a receptor as specific binding agent is also suitable, for example, steroids, halogens and 2,4 dinitrophenyl.

The preferred method for utilization of the invention is a process for the detection of "target" nucleic acid sequence which is characterized in that the sample is treated, after denaturation, with two distinct labeled oligonucleotides primers ($P_1$ and $P_2$). The first ($P_1$) is, in its sequence, complementary to a partial sequence of a strand of the target nucleic acid and is labeled with hapten ($H_1$). An additional primer ($P_2$) is complementary to another partial sequence of the target nucleic acid and labeled with a second hapten ($H_2$). The mixture is treated with polymerase, preferably Taq-polymerase, deoxyribonucleotide and subsequently repeating, at least once, the cycle consisting of denaturation, hybridization and polymerization. A double stranded nucleic acid results which is labeled with two distinct haptens at each 5' end. The resulting labeled nucleic acid is reacted with conjugated microparticles of suitable color and diameter for detection. The first of which is conjugated with a receptor ($R_1$) specific for binding at least one site on the first of the two distinct haptens ($H_1$). The second is conjugated with a receptor ($R_2$) specific for binding at least one site on the second hapten ($H_2$), the resulting microparticle bound amplicon is detected visually.

By way of example, cytomegalovirus is used as a PCR amplification target according to the PCR reaction and thermal cycling conditions disclosed by Gerdes (1993) *Transplantation Proceedings* 25:1411. PCR generated amplicons for bead detection utilize primers five-prime derivatized with either biotin or digoxigenin (Operon Technologies, Inc., Alameda, Calif.). Streptavidin coated 4.5 $\mu$m beads are obtained from Perkin Elmer (Foster City, Calif.) and anti-digoxigenin beads are made using anti-dig Fab obtained from Boehringer Mannheim (Indianapolis, Ind.) and covalently bound to Dynal (Great Neck, N.Y.) M-280 toxylactivated 2.8 $\mu$m beads. The PCR amplicon is run on agarose gel, cut out and purified with GeneClean (Bio 101, Alameda, Calif.) to eliminate possible primer dimers artifacts.

EXAMPLE 2

Microparticle Selection and Preparation

The preferred microparticles utilized in this invention are composed of polymeric materials such as latex polyethylene, polypropylene, polymethylmethacrylate or polystyrene. However, a variety of other synthetic or natural materials may also be used in the preparation of the microparticles, for example, silicates, paramagnetic particles and colloidal gold. The usual form of microparticle possesses sulfate charge groups on their surface but these surfaces can be modified by the introduction of functional groups such as hydroxyl, carboxyl, amine and carboxylate groups. The functional groups are used to bind a wide variety of ligands and receptors to the microparticles. These groups are selected on the basis of their ability to facilitate binding with the selected member of the ligand-receptor pair, either by covalent binding or adsorption. The preferred method of attachment of the receptor to the microparticles is covalent binding.

The size of the microparticles used in this invention is selected to optimize the binding and detection of the labeled amplicons. Microparticles are available in a size range of 0.02–100 $\mu$m in diameter. The preferred diameter for this embodiment of the invention is the range of 0.1–1.0 $\mu$m, specifically not excluding the use of either larger or smaller microparticles as appropriately determined. The microparticles are activated with a suitable receptor for binding to the target ligand. The preferred microparticle in the present invention is composed of latex containing a colored dye.

In the present invention, microparticle bound receptors are specific for discreet haptens located on the ends of amplified nucleic acid sequences. The receptors must be capable of binding to their specific binding partner (hapten) and, further changing the derivatized haptens from the preferred biotin and digoxigenin necessitates a change in the receptors. Conjugation of the receptors to the microparticle is accomplished by covalent binding or, in appropriate cases, by adsorption of the receptor onto the surface of the microparticle. Techniques for the adsorption or covalent binding of receptors to microparticles are well know in the art and require no further explanation.

In order to prepare the anti-digoxigenin coated microparticles, 0.25–1.0 mg/ml of anti-digoxigenin Fab is incubated with a suspension containing a final concentration of 1.0% microparticles/ml. The microparticles and digoxigenin Fab are allowed to react for 15 minutes prior to treatment with activating agent for covalent binding. The microparticles are treated with EDAC (1-ethyl-3-(3-dimethylaminopropyl)carbodiamide) at a final concentration of 0–2.5 mM. The Fab and microparticles are then mixed and incubated at room temperature for one hour. Unbound Fab is removed by successive washes and resuspended in storage buffer. The sensitivity of the coated microparticles is determined by: 1) agglutination reaction between secondary anti-body to digoxigenin Fab; 2) lateral flow assay; and 3) filtration assay. Inhibition of the reaction is demonstrated by pre-incubation with digoxigenin Fab and secondary antibody to digoxigenin Fab, prior to adding coated microparticles.

The microparticles are 0.3–10.0 μm in diameter. Three different carboxyl group densities and three different colors are evaluated for reactivity. The reactivity is evaluated by agglutination reactions, lateral flow membrane assay and filtration assay.

Agglutination reactions consist of adding 10 μl of each reactant to 10 μl of reaction buffer on a glass slide. The reaction is mixed gently and the rate of agglutination determined. Positive reactions show visible agglutination within 2 minutes and are rated on a 0 to +4 scale. Negative controls do not have visible agglutination within the specified time frame. Microparticles coated with non-specific protein or leaving the "bridging component" out of the reaction are used as negative controls.

Lateral flow membrane assays are performed on Biodyne C nylon membranes (Pall BioSupport Division, Port Washington, N.Y.) spotted with 1.0 μl streptavidin at concentrations between 0.0 and 1.0 mg/ml. Next, 25–75 μl of colored, biotinylated, coated beads, at dilutions of 0.001–1.0% microparticles/ml are allowed to wick up the membrane. A positive reaction results in a colored spot where the capture material is applied. Membranes spotted with 1.0 μl of buffer serve as negative controls. The membranes show background when soaked in a suitable blocking reagent, such as bovine serum albumin (BSA), "Tween-20" or Casein.

The filtration assays are accomplished by adding 10 μl of each reactant to 10 μl of reaction buffer in an ELISA well or microfuge tube, or spotting the reaction on a glass slide. The reaction proceeds for 2–10 minutes at room temperature. A 1.0–5.0 μl sample is removed from the reaction and spotted on a membrane filter, said filter being of a suitable pore size such that non-agglutinated microparticles pass through, but agglutinated microparticles cannot. The filter is then washed 2 times with phosphate buffered saline (PBS). Positive results are visible as colored "spots" on the filter, while negative results are not visible. That is, no colored "spots" are produced on the filters.

EXAMPLE 3

Target Nucleic Acid Amplicon Detection

The present invention includes the processes for the qualitative determination of specific target nucleic acid amplicons which have been bifunctionally labeled during amplification by incubating the hapten labeled target nucleic acid with at least two receptors, ($R_1$) and ($R_2$), whereby ($R_1$) and ($R_2$) are incapable of binding to each other and ($R_1$) and ($R_2$) are bound to dyed microparticles. The haptens disclosed herein, ($H_1$) and ($H_2$), are incapable of binding to each other. In the instant invention, ($R_1$) specifically binds to at least one site on ($H_1$) and ($R_2$) specifically binds to at least one site on ($H_2$). Detection of the target nucleic acid amplicon is accomplished in several ways as described below. Preferred receptors are streptavidin ($R_1$) and anti-digoxigenin antibody ($R_2$).

In a first embodiment, ($R_1$) and ($R_2$) conjugated dyed microparticles are added to a portion of the amplicon reaction mixture on a surface that does not bind any of the components of the assay, for example, a glass slide. The result, a linear and three dimensional cross-linkage of the amplicon. The resulting agglutination reaction is visible to the naked eye or by observation with an amplifying device such as a microscope. The reaction takes place in a matter of minutes. The specificity and sensitivity of the assay are determined by the primers. Agglutination can only take place if the target nucleic acid is present in the amplification mixture to form cross-links between the beads. If the target nucleic acid is not present, the dyed microparticles remain monodispersed and agglutination is not visible.

Figure 6A:
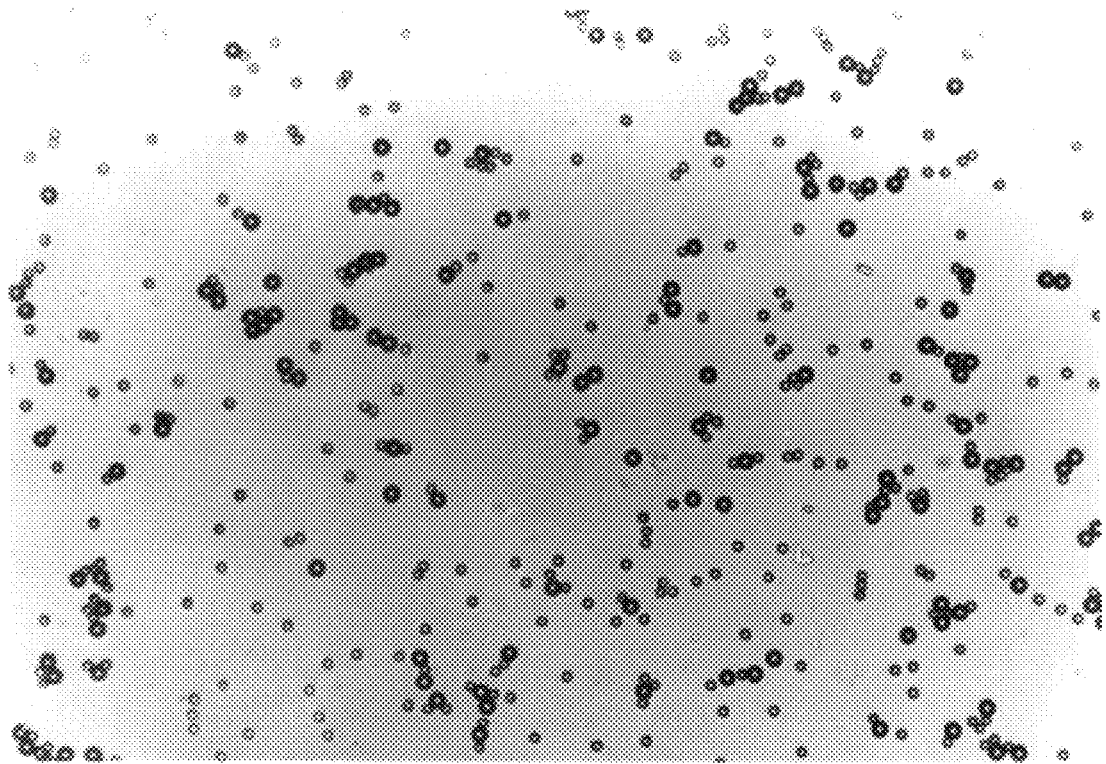
FIG. 6A depicts the microscopic view of glass slide agglutination reactions; the negative control shows no visible agglutination.
Figure 6B:
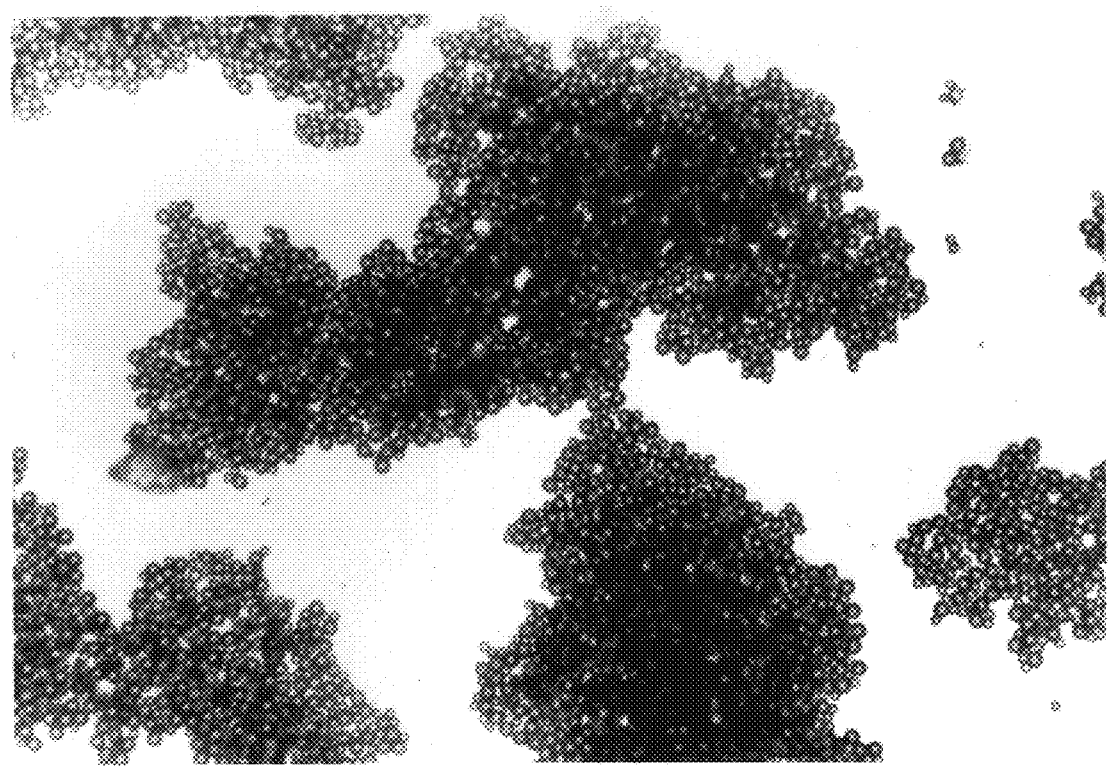
FIG. 6B depicts the microscopic view of glass slide agglutination reactions; visible agglutination indicative of positive results.
Figure 7:
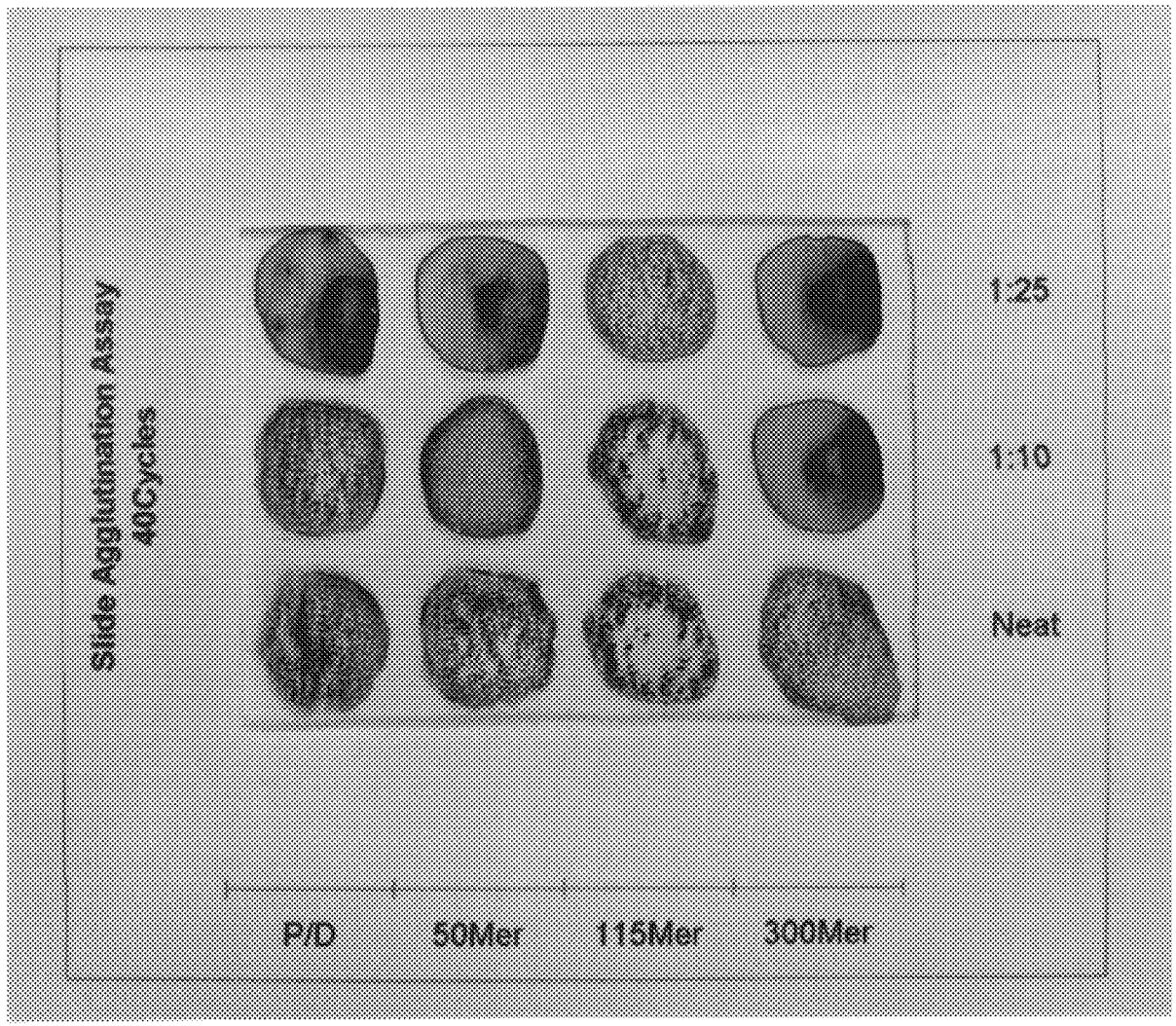
FIG. 7 depicts naked eye views of agglutination reactions. Visible agglutination is indicative of positive results; the negative control shows no visible agglutination.

Agglutination reactions consist of depositing 10 μl of 1% anti-digoxigenin coated microparticles, 10 μl of 1% streptavidin coated microparticles, 10 μl of reaction buffer and 10 μl of diluted HIV amplicon or buffer on a glass slide. The reaction is gently mixed and the rate of agglutination determined over a period of 2 minutes. Agglutination is visible in the reaction mix containing HIV amplicon. The negative control, containing buffer in place of amplicon, does not show agglutination. An additional negative control uses microparticles coated with non-specific protein. The results of such reactions are shown in FIGS. 6 and 7.

Another embodiment includes a method of detection relying upon filtration of the agglutination reaction through a porous membrane, said membrane having pores of a size such that unagglutinated microparticles flow through the membrane but agglutinated microparticles are retained on the filter as a visible "spot."

Filtration assays are performed by placing 10 μl of 1% anti-digoxigenin coated microparticles, 10 μl of 1% streptavidin coated microparticles, 10 μl of reaction buffer and 10 μl of diluted FHV amplicon or buffer in an ELISA well or microfuge tube, or spotting the reaction components on a glass slide. The reaction proceeds for 2–10 minutes at room temperature. A 1.0–5.0 μl sample is removed from the reaction and spotted on a membrane filter, said filter being of a suitable pore size such that nonagglutinated microparticles pass through but agglutinated microparticles cannot. The filter is then washed 2 times with PBS. Positive results are visible as colored "spots" on the filter, while negative results are not visible.

An alternative embodiment is to anchor one of the receptors ($R_1$) to a solid phase membrane. This group of receptors serves to capture the target sequence. The amplified nucleic acid is mixed with the second receptor ($R_2$) that is conjugated to a dyed microparticle. If the target nucleic acid is present in the reaction mix, ($R_2$) binds to ($H_2$) on the amplified nucleic acid. This mixture is then deposited on the membrane containing ($R_1$) and allowed to interact. If the target is present, the anchored receptor ($R_1$) interacts with hapten ($H_1$) to capture the amplified nucleic acid bound to the dyed microparticle through the interaction of ($H_2$) and ($R_2$). The result is a line of dyed particles visible on the membrane. If the target is not present, the dyed particle is not captured on the membrane, and thus, is not visible.

EXAMPLE 4

Lateral Flow Chromatography of Bifunctionally Labeled Human Immunodeficiency Virus (HIV) Amplification Product In the instant set of experiments, the primers, SK 38 and SK 39, are obtained from Operon, of Alameda Calif., and the derivatization methodology employed is outlined previously, in Example 1. The forward primer, SK 38, carries a 5' digoxigenin (dig) label. The reverse primer, SK 39, carries a biotin 5' label. The sequences of these primers are shown below:
SK 38 dig primer 5'-dig ATA ATC CAC CTA TCC CAG TAG GAG A SEQ ID NO:1

SK 39 biotin primer

5'-biotin TT TGG TCC TTG TCT TAT GTC CAG A SEQ ID NO:2

The sequence target for amplification of HIV, positions 1090 to 1205, is as follows:

5'ATAATCCACCTATCCCAGTAGGAGAAATTTATAAAAGATGGATAATCCTGGGATTAAATAAAATAGTAAG SEQ ID NO:3

AATGTATAGCCCTACCAGCATTCTGGACATAAGACAAGGACCAAA

Membrane used for this procedure is nitrocellulose, purchased from Millipore Corporation of Bedford, Mass. A stripe of streptavidin at a concentration of 1 mg/ml is applied at a rate of 1 µl/cm via a linear reagent striper (IVEK Corporation, No. Springfield, Vt.) 1 cm from the bottom edge of the membrane. After application of the streptavidin, the membrane is allowed to dry and then blocked for non-specific binding by 0.5% casein in 100 mM Tris, pH 7.4. The membranes are washed twice with water (ddH$_2$O) and allowed to dry. The microparticles used are prepared as outlined previously, in Example 2.

The target is amplified by PCR using 200–1000 mM primer concentration, GeneAmp EZ rTth RNA PCR kit (Perkin Elmer Corp., Alameda, Calif.) and $10^3$–$10^6$ copies/ml of the target sequence. Thirty to forty PCR cycles, each cycle being 60° C. for 15 minutes, 95° C. for 15 seconds, and 55° C. for 60 seconds, are run. The resulting amplicon is bifunctionally labeled during the PCR reaction with biotin and digoxigenin.

The amplicon (5 µl) is added to 5 µl of 0.1% anti-digoxigenin coated microparticles and 40 µl of water (ddH$_2$O), then applied (50 µl) to the previously striped membrane. The amplicon bound to the anti-digoxigenin microparticles wicks through the membrane to the streptavidin line and is captured by the interaction of biotin and streptavidin. The result is a visible line of colored microparticles.

Figure 9A:
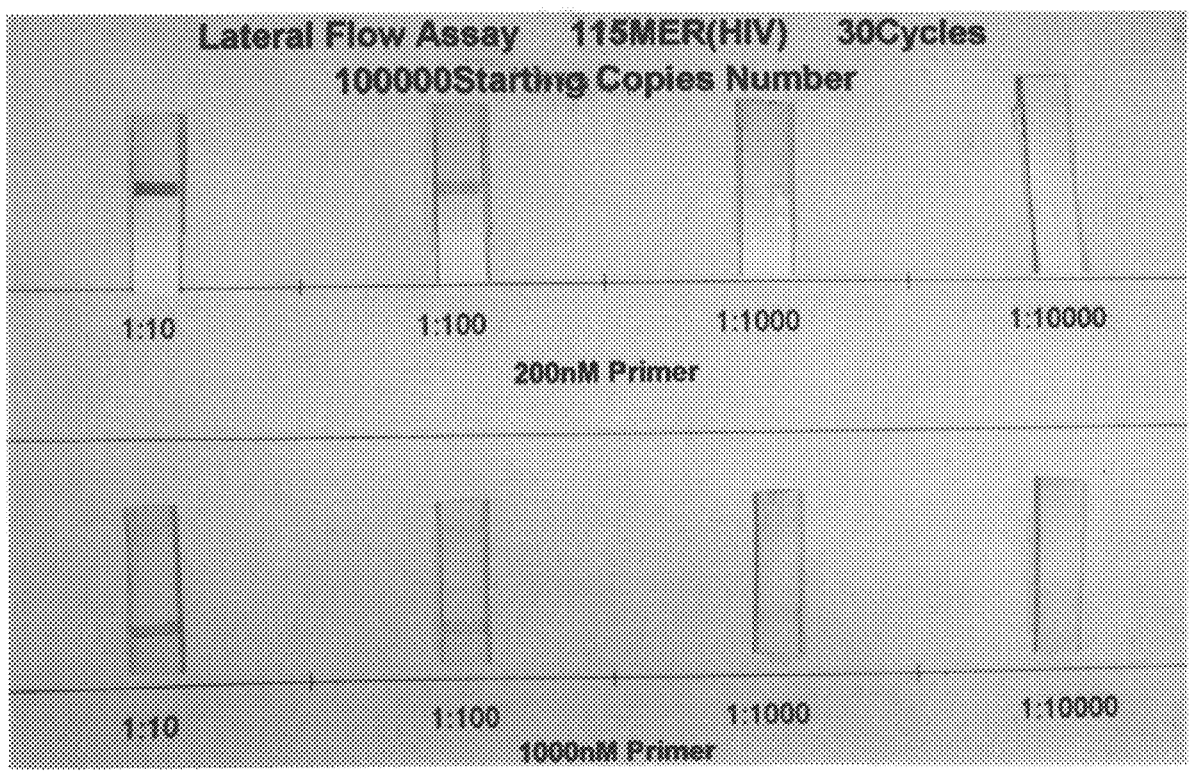
FIG. 9 depicts the results of lateral flow membrane assays of bifunctionally labeled amplification product. Positive results are shown as a visible line of colored microparticles captured on the membrane; a visible line of detection is not present in the negative control results.
Figure 9B:
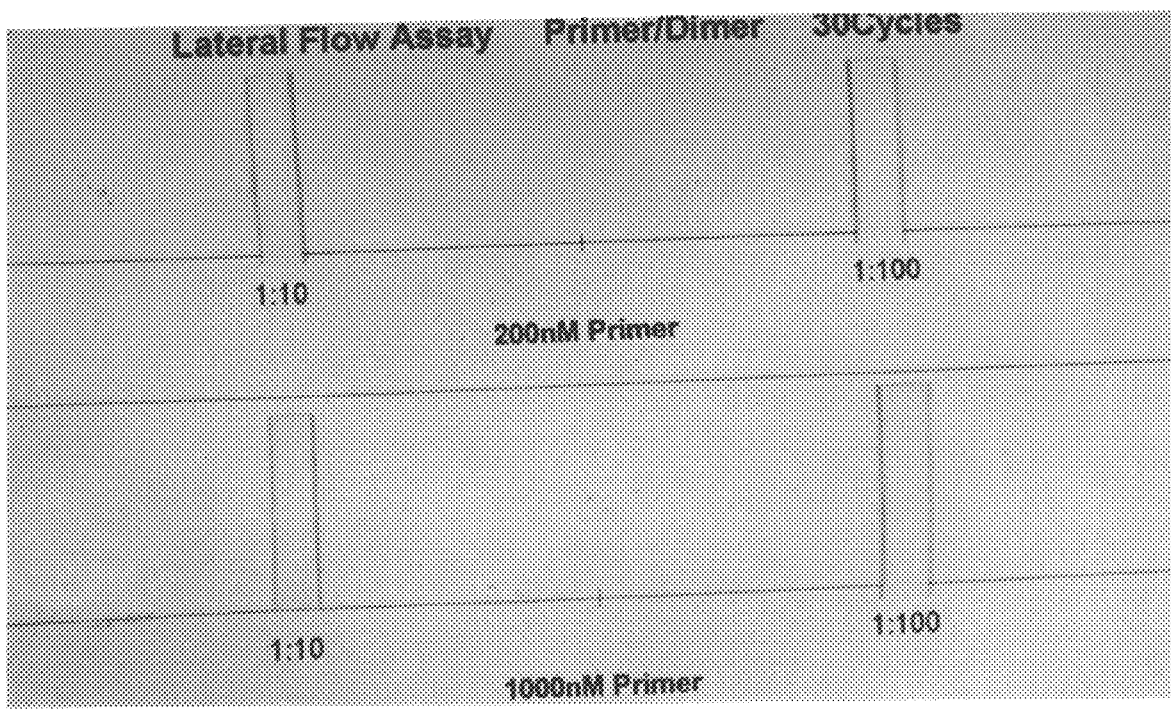
Figure 9:
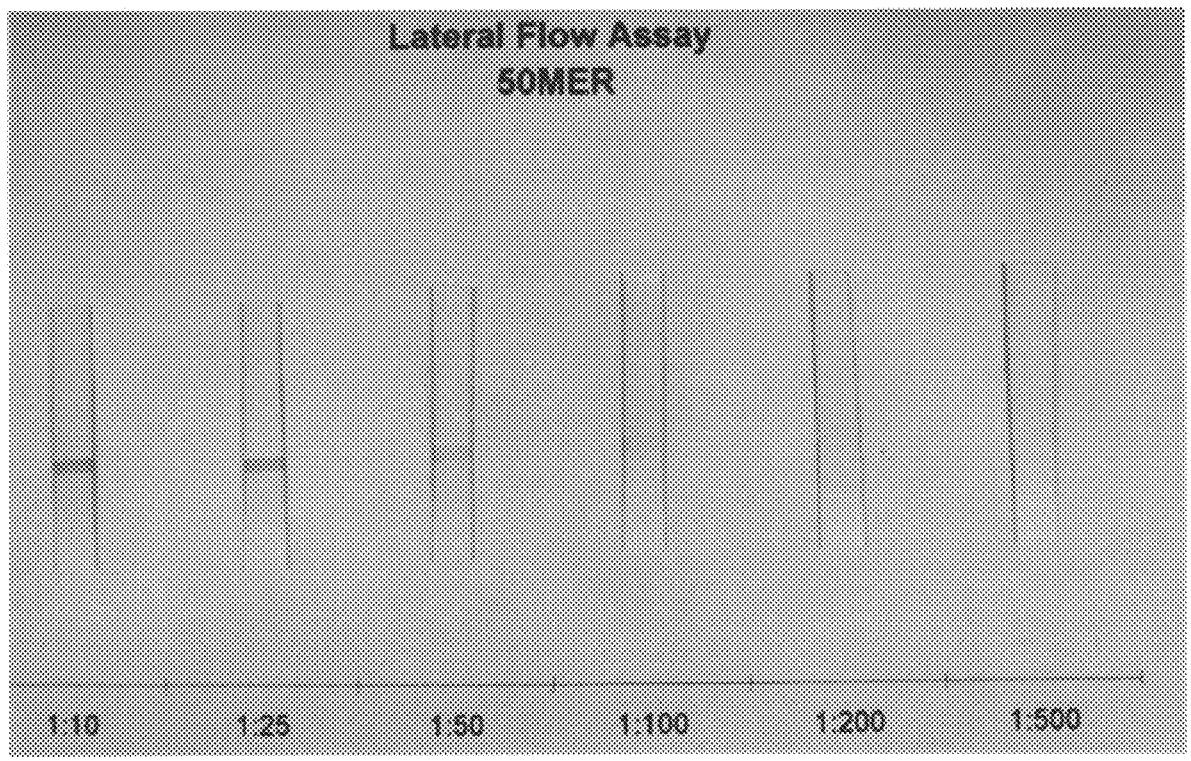

In the negative control, the procedure is performed as described above, but without the addition of the target sequence. Without the presence of the target sequence in the amplification reaction, the bifunctionally labeled amplicon is not generated and the visible line of detection is not present. The results of such experiments are shown in FIGS. 8 and 9.

EXAMPLE 5

Lateral Flow Chromatography of Bifunctionally Labeled Cytomegalovirus (CMV) Amplification Product The primers used in this set of experiments, MIEAN and MIEBN, are from Operon of Alameda, Calif. The derivatization methodology employed is outlined previously, in Example 1. The forward primer, MIEAN, carries a 5' digoxigenin label. The reverse primer, MIEBN, carries a biotin 5' label. The sequences of these primers are shown below:
MIEAN 5'digGCATTGAGGAGATCTGCATGAAGG    SEQ ID NO:4

MIEBN

5'biotinATTACTGAGGACAGAGGGATAGTC    SEQ ID NO:5

The sequence target for amplification of CMV is nucleotide 2758–3060.

Membrane used in this procedure is nitrocellulose, purchased from Millipore Corporation of Bedford, Mass. A stripe of streptavidin at a concentration of 1 mg/ml is applied at a rate of 1 µl/cm via a linear reagent striper (IVEK Corporation, No. Springfield, Vt.) 1 cm from the bottom edge of the membrane. After application of the streptavidin, the membrane is allowed to dry and then blocked for non-specific binding by 0.5% casein in 100 mM Tris, pH 7.4. The membranes are washed twice with water (ddH$_2$O) and allowed to dry. The microparticles used are prepared as outlined previously, in Example 2.

The target is amplified by PCR using 200–1000 mM primer concentration, GeneAmp EZ rTth RNA PCR kit (Perkin Elmer Corp., Alameda, Calif.) and $10^3$–$10^6$ copies/ml of the target sequence. Thirty to forty PCR cycles, each cycle being 60° C. for 15 minutes, 95° C. for 15 seconds, and 55° C. for 60 seconds, are run. The resulting amplicon is bifunctionally labeled during the PCR reaction with biotin and digoxigenin.

The amplicon (5 µl) is added to 5 µl of 0.1% anti-digoxigenin coated microparticles and 40 µl of water (ddH$_2$O), then applied (50 µl) to the previously striped membrane. The amplicon bound to the anti-digoxigenin microparticles wicks through the membrane to the streptavidin line and is captured by the interaction of biotin and streptavidin. The result is a visible line of colored microparticles.

In the negative control, the procedure is performed as described above, but without the addition of the target sequence. Without the presence of the target sequence in the amplification reaction, the bifunctionally labeled amplicon is not generated and the visible line of detection is not present.

EXAMPLE 6

Agglutination of HIV Amplification Product Using One Labeled Primer and One Unlabeled Primer. Followed by Hybridization with a Second Labeled Probe in Order to Create a Bifunctionally Labeled Amplicon The primers, SK 38 and SK 39, and the sequence target for amplification of HIV used in this example are identical to those described in Example 4 (SEQ ID NOS: 1–3). Furthermore, the derivatization methodology is outlined previously, in Example 1. The sequence of the 61 mer probe employed in this example is as follows:

61 mer probe

```
5'-(Biotin)GCT GGT AGG GCT ATA CAT TCT TAC TAT TTT ATT   SEQ ID NO:6
TAA TCC CAG GAT TAT CCA TCT TTT ATA A-3'
```

The target is amplified by PCR using 200–1000 mM primer concentration, GeneAmp EZ rTth RNA PCR kit (Perkin Elmer Corp., Alameda, Calif.) and $10^3$–$10^6$ copies/ml of the target sequence. Thirty to forty PCR cycles, each cycle being 60° C. for 15 minutes, 95° C. for 15 seconds, and 55° C. for 60 seconds, are run. The resulting amplicon is labeled only with biotin during the PCR reaction.

Following amplification, 5 µl of SK 38 Dig - - - SK 39 single labeled product is added to 5 µl of 25 µl (125 pmol) SK 39 labeled with biotin. The mixture is heated to 95° C. for 1 min, then cooled to 55° C. for 1 min. Alternatively, 5 µl of 1:2 dilution in water of the SK 38 Dig - - - SK 39 single labeled product is added to 5 µl of 2.5 µM HIV 61 mer biotin labeled probe. The mixture is heated to 95° C. for 1 min, then cooled to 60° C. for 1 min. The hybridization step constructs a product that is bifunctionally labeled.

The microparticles are prepared as outlined previously, in Example 2. hybridized product to 5 µl anti-dig coated microparticles (0.2%) and 5 µl streptavidin coated microparticles (0.2%). The results of a hybridization test containing a target sequence are a visible agglutination of the microparticles. Samples that do not contain a target sequence do not agglutinate and samples that are not bifunctionally labeled with the hybridization step also do not agglutinate.

EXAMPLE 7

Inhibition Assay: Loss of Visible Signal on Lateral Flow Membrane

The specific probe and target employed in the instant example have been designed by ID Biomedical Corporation for use in detecting *Mycobacterium tuberculosis*. The probe is a chimeric construct containing both DNA and RNA sequences with labels on the 5' (fam) and the 3' (biotin) ends of the DNA portion of the probe. The binding of the probe to a single strand of target generates double stranded nucleic acid which is cleaved with RNase H, thus, eliminating the bifunctionality of the probe. The sequence of the probe is described below:

FARK2S3B probe

```
5'-[SEQ ID NO:7] (lowercase letters are 2'-O-ribonucleoside bases)
```

The sequence of the target is described below:
ARK2-T synthetic target

```
5'-AAT CTG TAC CCT CTA CAT CTT TAA-3'    SEQ ID NO:8
```

The reaction is completed following the protocol provided by ID Biomedical Corporation.

Membrane used for this procedure is nitrocellulose, purchased from Millipore Corporation of Bedford, Mass. A stripe of streptavidin at a concentration of 1 mg/ml is applied at a rate of 1 µl/cm via a linear reagent striper (IVEK Corporation, No. Springfield, Vt.) 1 cm from the bottom edge of the membrane. After application of the streptavidin, the membrane is allowed to dry and then blocked for nonspecific binding by 0.5% casein in 100 mM Tris, pH 7.4. The membranes are washed twice with water (ddH$_2$O) and allowed to dry. The microparticles used are prepared as outlined previously, in Example 2, replacing anti-digoxigenin Fab with anti-fam monoclonal IgG.

The reaction product (10 µl) is added to 5 µl of 0.1% anti-fam coated microparticles (0.1%) and 35 µl of water (ddH$_2$O), then applied (50 µl) to the previously striped membrane. The binding of the probe to the target followed by cleavage of the probe by RNase H, results in loss of the bifunctionality of the probe. When the target is present, the absence of a visible line on the membrane exists. When the target is not present, the bifunctionally labeled probe is able to bind the anti-fam coated microparticles and the streptavidin bound to the membrane, resulting in a visible line.

EXAMPLE 8

Isothermal Amplification Approach to Detection with Bifunctionally Labeled Amplified Target Sequence The instant strand displacement assay (SDA) is an example of an isothermal amplification that can be detected by using microparticles and bifunctionally labeled product. SDA technology is described in U.S. Pat. No. 5,455,166 to Becton Dickinson and Company, specifically incorporated herein.

This set of experiments is conducted with composite extension primers that are labeled with biotin, fam or digoxigenin. Bumper primers are the same sequence as provided by Becton Dickinson and Company (Franklin Lakes, N.J.). The sequences of the target, the bumper primer and the composite extension primer are as follows:

Bumper primers:

| | |
|---|---|
| B1: 5'-CGATCGAGCAAGCCA | SEQ ID NO:9 |
| B2: 5'-CGAGCCGCTCGCTGA | SEQ ID NO:10 |

Composite extension primers:

| | |
|---|---|
| S1: 5'-fam/dig-ACCGCATCGAATGCATGTCTCGGGTAAG-GCGTACTCGACC | SEQ ID NO:11 |
| S2: 5'-biotin-CGATTCCGCTCCAGACTTCTCGGGTG-TACTGAGATCCCCT | SEQ ID NO:12 |

Target sequence:

```
5'TGGACCCGCCAACAAGAAGGCGTACTCGACCTGAAAGACGTTATCCACCAT   SEQ ID NO:13
ACGGATAGGGGATCTCAGTACACATCGATCCGGTTCAGCG
```

The reaction is set up per the thermophilic Strand Displacement Amplification (tSDA) protocol developed by Becton Dickinson and Co. The target organism is *Mycobacterium tuberculosis*. For pilot studies, an artificial target template consisting of the 91nt sequence of the *M. tuberculosis* genome, defined by the Becton Dickinson outer (bumper) primers, is used. Amplification conditions used are identical to those used by Becton Dickinson for tSDA.

Membrane used for this procedure is nitrocellulose, purchased from Millipore Corporation of Bedford, Mass. A stripe of streptavidin at a concentration of 1 mg/ml is applied at a rate of 1 µl/cm via a linear reagent striper (IVEK Corporation, No. Springfield, Vt.) 1 cm from the bottom edge of the membrane. After application of the streptavidin, the membrane is allowed to dry and then blocked for non-specific binding by 0.5% casein in 100 mM Tris, pH 7.4. The membranes are washed twice with water (ddH$_2$O) and allowed to dry. Next, 3 µl of anti-S1 (complementary to S1 without the biotin label) and/or S2 primer (complementary to S2 without the dig or fam label) is spotted onto a second membrane. This membrane is sandwiched onto the first membrane in order to capture free primers that compete with the product for the microparticles or streptavidin capture zone. The microparticles used are prepared as outlined previously, in Example 2, with either anti-digoxigenin Fab or anti-fam monoclonal IgG. The microparticles are diluted 1:2 with a 35% sucrose solution and 3 µl applied directly to the membrane and dried.

The reaction product (10 µl) is added to 45 µl SDA buffer, then applied (50 µl) to the previously striped membrane. Application of the sample requires the bifunctionally labeled product and the competing primers to pass through the anti-primer coated membrane and the dried microparticles. When the target is present, there is a visible line on the membrane. When the target is not present, there is absence of a visible line.

Tests kits for the detection of target nucleic acid sequence determination that include hapten labeled primers, enzymes or ligases, nucleosides and receptor bound dyed microparticles are envisioned. Depending upon the detection method employed in each test kit, also included in the appropriate kit will be microscope slides, microporous membrane/filtration apparatus or microporous membrane/dip stick apparatus.

The instant invention provides a rapid, simple and accurate method of detecting amplified target nucleic acid sequences with a visual signal. The sensitivity and specificity of the assay are not based on hybridization but on the bifunctional labeling of the target during the amplification process. The method is as sensitive as current methodologies utilizing enzymes and fluoureceins. The method does not require costly and sophisticated equipment or specially trained personnel and it does not pose a health hazard.

While the above description contains many specificities, these specificities should not be construed as limitations on the scope of the invention, but rather an exemplification of the preferred embodiment thereof. That is to say, the foregoing description of the invention is exemplary for purposes of illustration and explanation. Without departing from the spirit and scope of this invention, one skilled in the art can make various changes and modifications to the invention to adapt it to various usages and conditions. For example, other variations may include amplifying several target samples in the same reaction mixture, amplifying with ligase chain reaction, etc. As such, these changes and modifications are properly, equitably, and intended to be within the full range of equivalence of the following claims. Thus the scope of the invention should be determined by the appended claims and their legal equivalents, rather than by the examples given.

I claim:

1. A method for the detection of amplified target nucleic acid sequences which comprises:
   a) denaturing a multiple stranded nucleic acid to produce a single stranded nucleic acid or beginning with a single stranded nucleic acid;
   b) amplifying the target nucleic acid sequence with a first hapten derivatized complementary primer and dNTP and a second hapten derivatized complementary primer and dNTP to produce bifinctionally labeled specific target nucleic acid amplicons;
   c) contacting dyed microparticles conjugated to a first hapten specific receptor corresponding to said first primer, dyed microparticles conjugated to a second hapten specific receptor corresponding to said second primer and said labeled target nucleic acid sequence wherein an agglutination reaction forms agglutination product of the amplified target nucleic acid; and
   d) detecting the resulting agglutination product.

2. The method of claim 1 wherein the primers are derivatized with biotin.

3. The method of claim 1 wherein the primers are derivatized with biotin and digoxigenin.

4. The method of claim 1 wherein the primers are derivatized with biotin and fam.

5. The method of claim 1 wherein the primers are derivatized with biotin, fam or digoxigenin.

6. The method of claim 1 wherein the primers are derivatized with haptens selected from the group consisting of steroids, halogens and 2,4 nitrophenyl.

7. The method of claim 1 wherein the amplification target is any specific nucleic acid sequence.

8. The method of claim 3 wherein the amplification target is nucleic acid sequences for Cytomegalovirus.

9. The method of claim 3 wherein the amplification target is nucleic acid sequences for Human Immunodeficiency Virus.

10. The method of claim 5 wherein the amplification target is nucleic acid sequences for *Mycobacterium tuberculosis*.

11. The method of claim 1 wherein the target nucleic acid is amplified isothermally.

12. The method of claim 1 wherein the dyed microparticles are covalently bound to hapten specific receptors.

13. The method of claim 1 wherein the amplified target nucleic acid is contacted with receptor bound dyed microparticles during amplification.

14. The method of claim 1 wherein the dyed microparticles are attached to the receptors via adsorption to the microparticles' surface.

15. The method of claim 12 wherein the bound receptors are streptavidin and anti-digoxigenin antibody.

16. The method of claim 12 wherein the bound receptors are streptavidin and anti-fam antibody.

17. The method claim 1 wherein the microparticles are 0.02–10.0 micrometers in diameter.

18. The method of claim 1 wherein the microparticles are 0.1–1.0 micrometers in diameter.

19. The method of claim 1 wherein the microparticles are composed of an insoluble polymer material.

20. The method of claim 19 wherein the insoluble polymer material is latex.

21. The method of claim 19 wherein the insoluble polymer material is selected from the group consisting of polyethylene, polypropylene, polymethylmethacrylate and polystyrene.

22. The method of claim 1 wherein the microparticles are composed of colloidal gold.

23. The method of claim 1 wherein said agglutination product is detected using a secondary detection probe capable of binding to said microparticles.

24. The method of claim 23 wherein the secondary detection probe is an anti-species antibody.

25. The method of claim 1 wherein said detection is made by a method selected from the group consisting of agglutination observation, lateral flow membrane assay and filtration assay.

26. A kit for the amplification and detection of a target nucleic acid consisting essentially of:
   a) target specific hapten labeled primers;
   b) thermostable polymerase;
   c) dNTPs; and
   d) receptor bound dyed microparticles.

27. The kit of claim 26 further consisting of agglutination product detection apparatus.

28. The kit of claim 27 wherein the agglutination product detection apparatus is microporous membrane.

29. The kit of claim 28 wherein the membrane is nitrocellulose or nylon.

30. The kit of claim 29 wherein the membrane has a receptor immobilized thereon.

* * * * *

UNITED STATES PATENT AND TRADEMARK OFFICE
CERTIFICATE OF CORRECTION

PATENT NO. : 5,989,813  
DATED : November 23, 1999  
INVENTOR(S) : John C. Gerdes Page 1 of 1

It is certified that error appears in the above-identified patent and that said Letters Patent is hereby corrected as shown below:

Column 1,
Line 4, please insert the following paragraph:
-- CONTRACTUAL ORIGIN OF THE INVENTION
This invention was made with United States Government support under cooperative agreement number 70NANB5H1109 awarded by the National Institute of Standards and Technology (NIST). The United States Government has certain rights in the invention. --

Signed and Sealed this

Twenty-ninth Day of June, 2004

JON W. DUDAS
*Acting Director of the United States Patent and Trademark Office*